Figure 1:
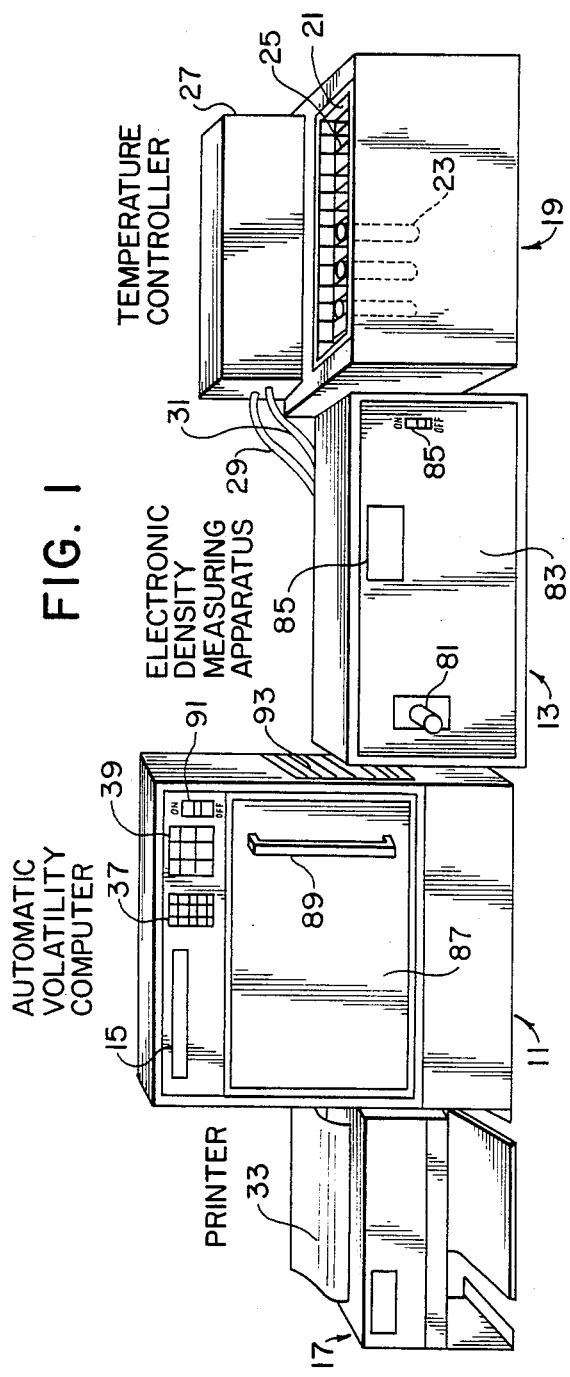

United States Patent [19]

Collins et al.

[11] Patent Number: 4,566,312

[45] Date of Patent: Jan. 28, 1986

[54] APPARATUS AND PROCESS FOR AUTOMATICALLY DETERMINING FAT CONTENTS OF FOODS

[75] Inventors: Michael J. Collins, Matthews; Ronald J. Goetchius, Charlotte, both of N.C.

[73] Assignee: CEM Corporation, Matthews, N.C.

[21] Appl. No.: 606,352

[22] Filed: May 2, 1984

[51] Int. Cl.⁴ .................. G01N 9/04; G01N 25/56
[52] U.S. Cl. .................... 73/32 A; 73/76; 73/432 R; 364/496; 374/14
[58] Field of Search ............... 73/32 R, 32 A, 76; 374/14, 54; 364/558, 567, 496

[56] References Cited

U.S. PATENT DOCUMENTS

| | | | |
|---|---|---|---|
| 1,396,743 | 11/1921 | Gray | 73/448 |
| 3,523,446 | 8/1970 | Kratky | 73/32 A |
| 3,557,625 | 1/1971 | Leger, Jr. et al. | 73/32 |
| 3,909,598 | 9/1975 | Collins | 73/76 |
| 3,910,101 | 10/1975 | Kratky | 73/32 A |
| 4,144,804 | 3/1979 | O'Keefe | 99/452 |
| 4,145,450 | 3/1979 | Winder | 73/61 R |
| 4,170,128 | 10/1979 | Kratky et al. | 73/32 A |
| 4,266,425 | 5/1981 | Allport | 73/61 R |
| 4,291,775 | 9/1981 | Collins | 73/76 |
| 4,359,638 | 11/1982 | Allport | 73/61 R |

Primary Examiner—S. Clement Swisher
Attorney, Agent, or Firm—Raymond F. Kramer

[57] ABSTRACT

Apparatuses and processes are described for the automatic determinations of fat contents of foods, such as dairy products, e.g., milk, wherein automatic density and solids content determining apparatuses are employed, together with a computer, to determine the fat contents of food samples being tested. The density determining apparatus is preferably one which is electromagnetically excited to vibrate at its natural resonant frequency, so that from the change in such frequency, compared to a control, the mass of the sample may be determined. The means for measuring the solids content is preferably an automatic volatility computer in which electromagnetic radiation (microwave energy) is employed to drive off the volatile material (usually mostly water) in the sample, which is automatically weighed before and after such volatilization. Preferably, a microcomputer in the automatic volatility computer is employed to compute fat content from electronic feeds to it from the density and the solids content determining apparatuses.

18 Claims, 3 Drawing Figures

APPARATUS AND PROCESS FOR AUTOMATICALLY DETERMINING FAT CONTENTS OF FOODS

This invention relates to apparatuses and processes for automatically determining fat contents of foods. More particularly, it relates to such apparatuses and related processes which are especially useful for determining the fat contents of dairy products, such as milk, which apparatuses and processes automatically measure product density and total solids content, and from such measurements, which are automatically electronically transmitted to a computer, such as a microprocesser, compute and report or record the fat content of the sample.

It is often desirable to be able to determine quickly the percentage of a particular chemical component in a sample of material. It is important to be able to make such a rapid determination of the content of a component in a product being continuously manufactured, especially when such a product has specification set for it on the maximum and/or minimum permitted content of such a component. Thus, for example, by knowing the fat content of milk being processed in a dairy, one is able to be assured that the product meets specifications for fat, and if it doesn't steps can be taken to blend the product with another milk of different characteristics to make on-specification material. With rapid analysis being possible, as by the method of this invention, utilizing the apparatus thereof, over-specification products, which might otherwise be manufactured to avoid noncompliance with requirements for minimum contents of components, may be avoided, and economies in manufacturing operations may be achieved.

Because chemical tests and conventional extraction procedures for determining the contents of fats in dairy products and in other products, and for determining the contents of other components in various materials, have often been time consuming, efforts have been made to accelerate the testing procedures. For example, the solvent extraction of fats (and oils) from materials, such as butter, margarine, salad dressings and meats, has been mechanized, utilizing high speed mechanical agitation to effect rapid solvent extraction, and the solvent has been automatically redistilled so that it may be reused. An apparatus that accomplishes this, the CEM Fat Analyzer and/or the CEM Fat/Oil Analyzer, is manufactured by CEM Corporation, Indian Trail, N.C., and when used in conjunction with a moisture/solids analyzer made by the same company, typically provides a moisture and fat content analysis of a small sample of a product within about 6 to 8 minutes, with such analytical results being reported on a display screen of the moisture/solids analyzer. Such fat and oil analyzing apparatus is described in U.S. patent applications of Michael J. Collins, Ser. No. 021,986, filed Mar. 19, 1979, and Ser. No. 445,199, filed Nov. 29, 1982, and in a bulletin entitled The CEM Fat Analyzer, copyrighted in 1981 by CEM Corporation.

Although the speedier solvent extraction technique mentioned above has advanced the analytical art significantly, sometimes it has been considered to be preferable to avoid the employment of extraction solvents. Use of such solvents may be objected to by some for economic, environmental and health reasons. Also, because some of the fats present in dairy products (often about 20%) is tightly bound and not readily removable by single solvent extraction, a plurality of solvents or special treatments may be needed, with resulting complications of the extraction apparatus and process. For those and/or other reasons, efforts have been made to employ other techniques, preferably physical or mechanical, and different from chemical and extraction operations. A search in the U.S. Patent and Trademark Office has resulted in the finding of the following patents, which relate to various techniques for the analyses of materials, such as foods, for particular components, such as fats and oils: U.S. Pat. Nos. 2,166,842; 3,433,057; 3,455,168; 3,523,446; 3,537,820; 3,557,625; 3,813,918; 3,909,598; 3,910,101; 4,144,804; 4,145,450; 4,170,128; 4,266,425; 4,287,760; 4,291,775; and 4,359,638. Of the mentioned U.S. Pat. Nos. 3,909,598 and 4,291,775, both of which are owned by the assignee of the present application, relate to computerized microwave analytical dryers (or automatic volatility computers). U.S. Pat. Nos. 3,523,446; 3,910,101; 4,170,128 relate to apparatuses for measuring densities of liquids by determining the resonant frequency of a container of the liquid being tested. U.S. Pat. Nos. 4,144,804; 4,145,450; 4,266,425; and 4,359,638 describe apparatuses and processes for determining the fat contents of dairy products by physical or electrophysical methods. In addition to the mentioned patents, also relevant are various booklets, manuals and bulletins issued by CEM Corporation, manufacturer of the automatic volatility computer, and Anton Paar K.G. (of Graz, Austria), manufacturer of the density determining equipment. Among such the most relevant are considered to be: the CEM Corporation operation and service manual entitled Automatic Volatility Computer, Model AVC ™-80, copyrighted in 1982 and reprinted in August, 1983; the CEM Corporation bulletin entitled Moisture/Solids Analyzer, AVC-80, copyrighted in 1981; and an instruction manual and a bulletin, both from Anton Paar K.G., and both entitled Digital Density Meter, DMA-40, according to O. Kratky, H. Leopold and H. Stabinger (no copyright or publication dates indicated).

Although the various patents and publications indicate that efforts have been made to accurately and quickly measure the fat contents (and contents of other components) of various materials, especially foods, such as dairy products and meats, and that various mechanical, physical, electrical and electronic means have been employed in such attempts, and although apparatuses are known that are capable of automatic moisture determination by microwave heating, with automatic weighings and computer reporting of the moisture and/or solids content on a display and for density determination by means of measurement of the resonant frequency or period of an oscillator formation including the sample being tested, with computer calculation of density from such data and reporting of the density on a display, before the present invention the fat content of a dairy product had not been determined by means of a combination of means for automatically producing an electronic signal corresponding to the density of a dairy product with means for automatically producing an electronic signal corresponding to the solids content of the dairy product, and utilizing a computer to calculate the fat content of the dairy product from the relevant signals and automatically to display, print, transmit and/or store such result. By means of the present invention the fat contents of dairy products, as well as contents of comparable components of other materials, may be rapidly and accurately determined from small samples of such materials, thereby facilitating rapid evaluations, production controls and standardizations of such materials, leading to important savings of time and money.

In accordance with the present invention an apparatus for determining the fat content of a food comprises means for automatically measuring a density characteristic of a food and producing an electronic signal corresponding to the density of the food, means for automatically measuring a solids content characteristic of a food and producing an electronic signal corresponding to the solids content of the food, computer means to determine the fat content of the food from the electronic signals, means for transmitting the electronic signals to the computer means, and means for reporting the fat content of the food. Preferably, the apparatus is adapted to determine the fat content of dairy products, such as milk, cream, condensed milk, ice cream mixes, ice cream and cottage cheese, by use of a density determining apparatus which includes a mechanical oscillator formation containing a sample of the dairy product, in liquid state, and an automatic volatility computer for determining the moisture and/or solids content of the sample of the dairy product. Although a separate computer can be employed to convert the electronic signals from both apparatus components to a readable display or print-out of the fat content of the sample, the computer will preferably be located in either the density or volatility apparatus, more preferably in the latter. It is also preferable for the computer to be programmed, as by a plurality of circuits in a chip or in a plurality of chips, so as to be capable of selectively computing fat contents of different types of dairy products, and sometimes, of other materials, too.

Also within the invention is a process for determining the fat content of a food which comprises automatically measuring a density characteristic of a food and producing an electronic signal corresponding to the density of the food, automatically measuring a solid content characteristic of a food and producing an electronic signal corresponding to the solids content of the food, transmitting the electronic signals to a computer, automatically computing with the computer the fat content of the food from the electronic signals, and reporting the fat content of the food. The temperature of the sample undergoing density measurement is normally in the range of 10° to 55° C., preferably 30° to 50° C. and more preferably 35° to 45° C., and the temperature, as charged, of the sample for volatiles, moisture or solids determination is within the range of 1° to 30° C., preferably 2° to 10° C., e.g., about 5° C. Preferably the density characteristic measured is the period but frequency or other relatable property can be measured instead. Similarly, instead of solids content moisture content may be employed. In such cases the computer instructions will be modified accordingly. For simplicity various references herein will be to period as the characteristic corresponding to density, and to solids content, but utilizing frequency and volatiles content are also within the described invention.

Figure 3:
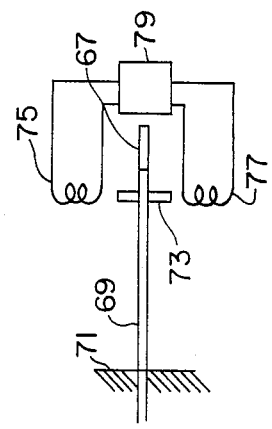
Figure 2:
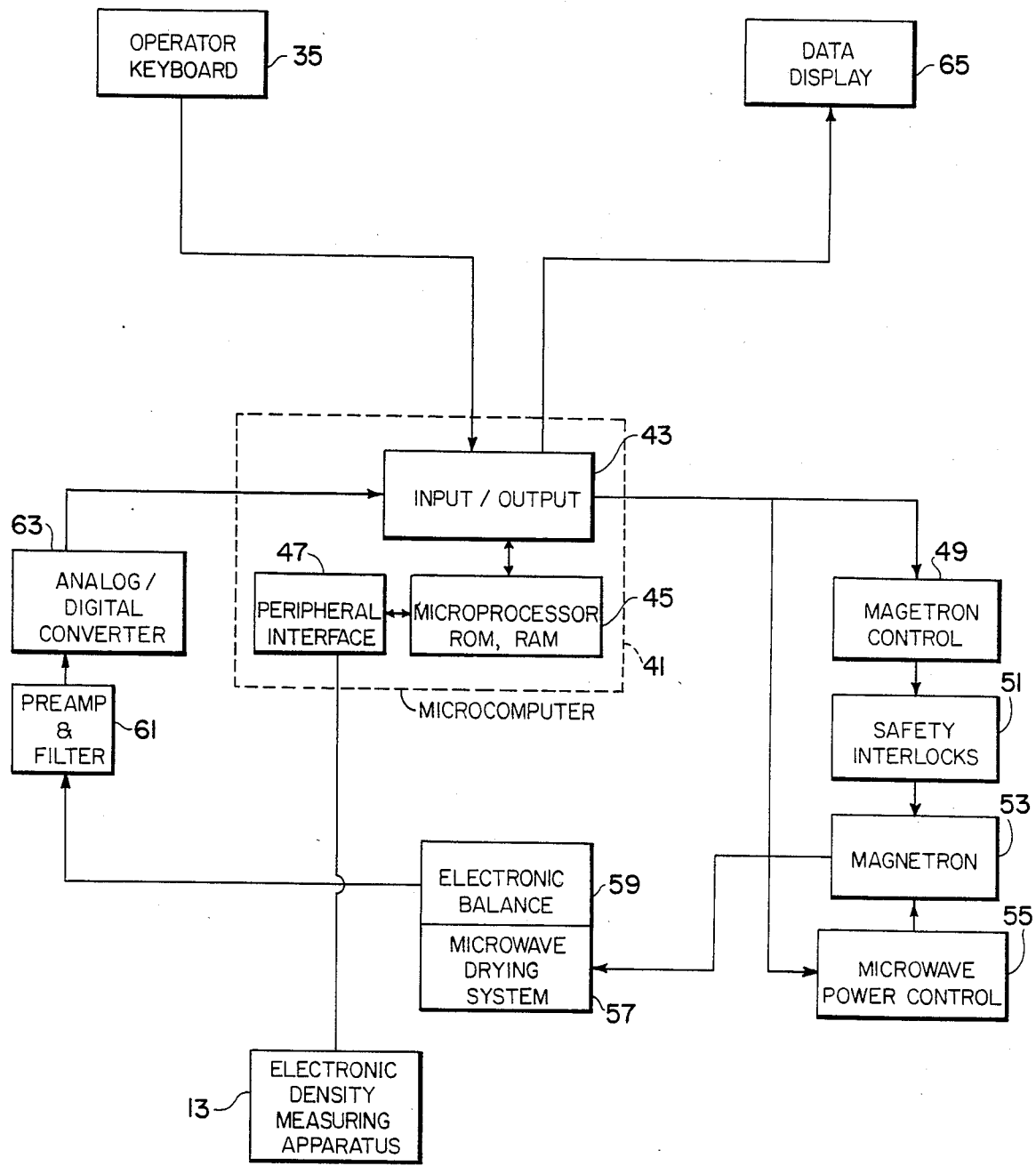

The invention will be readily understood by reference to this specification, including illustrative working examples thereof, taken in conjunction with the drawing, in which FIG. 1 is a front perspective view of the apparatus of this invention;

FIG. 2 is a schematic diagram of the components of the automatic volatility computer portion of this invention, shown interfacing with the electronic density measuring apparatus; and FIG. 3 is a diagrammatic elevational view of the mechanical oscillator (or mechanical oscillator formation) of the density determining device portion of this invention.

In the embodiment of the invention illustrated in FIG. 1 automatic volatility computer 11 includes a microprocessor (see FIG. 2) which measures weights of a test sample before and after evaporation of volatiles from it, caused by microwave radiation, and computes and reports the solids or volatiles (or moisture, in many cases) content of the sample. Electronic density measuring apparatus 13 is electronically connected to the microcomputer (and microprocessor) of the automatic volatility computer. Electronic signals characteristic of the density (periods) from such density measuring apparatus are transmitted to the microcomputer and from such signals and signals characteristic of the volatiles (or moisture) content or of the solids content, from the automatic volatility computer, the fat content (or a content of comparable material) of the dairy product (or other product) is determined and is displayed by the automatic volatility computer in display 15 and/or printed by printer 17.

Temperature controller 19 acts to control the temperature of water or other heat transfer liquid (not shown) in well 21 thereof, in which containers or vials 23 are held, supported by cage-like holder 25. Containers 23 hold sample liquids which are being tempered prior to being inserted into the electronic density measuring apparatus 13. The temperature controller also includes a second portion or section 27 in which the temperature of the water bath is controlled so that water at a controlled temperature may be delivered from section 27 through delivery line 29 to density measuring apparatus 13, wherein it controls the temperature of the sample, in liquid state, of material to be tested (in which apparatus such material's density or a characteristic thereof will be measured). The temperature controlled water delivered by tube 29 will be returned to temperature controller 19 (section 27 thereof) via line 31. Temperature controller 19 is very desirably one which accurately controls the temperature of the circulating water and that in the well 21. Usually such control will be to within 0.5° C. of the desired temperature, preferably to within 0.2° C. and more preferably to within 0.1° C. or 0.05° C. Normally the same water will circulate in both sections of the controller but at other times it may be preferable to utilize separated volumes of water or other heat transfer medium. Within the temperature controller, but not shown, may be a mixer or circulator, a pump, a thermostat or a plurality of thermostats, and means for adjusting the rate of flow of heat transfer medium from the temperature controller to the density measuring apparatus (pinch clamps can be used for such purpose).

Printer 17 may be of any suitable type. It is electronically connected to the computer of the apparatus, which will preferably be incorporated in the automatic volatility computer unit 11 (but can be separate or in the density measurer). The printer will usually print in response to a print instruction or may be set to print some or all of the operation of the apparatuses, such as the materials appearing at display 15, which materials can be printed on continuous paper sheet 33.

In FIG. 2, in which the automatic volatility computer parts and functions are illustrated schematically, operator keyboard 35, which incorporates numeric and function input keys or equivalent synthetic plastic film covered activator sections 37 and 39 (FIG. 1), allows the operator to input the microcomputer of the automatic volatility computer 11. The various inputs are numerals 1 through 9 and 0, and recall and water/solids functions in area 37, with the remaining functions, set power, set time, stop test, mode, change, clear, ready, tare and run, being in function area 39, but other arrangements are also practicable. After inputting the microcomputer 41 by means of input/output section 43 thereof, the input signals are fed to microprocessor 45 and to peripheral interface 47, which is normally optional in such an automatic volatility computer but is present in the present apparatus because of the need to interface with the density measuring apparatus 13. In addition, peripheral interface 47 may allow interfacing with communication lines, other computers and storage. Input/output area 43 also communicates with magnetron control 49, safety interlock 51, magnetron 53 and microwave power control 55, in the manner illustrated in FIG. 2. Activation of the magnetron causes electromagnetic radiation to enter the microwave cavity portion 57. Electronic balance 59, the pan of which is in the microwave cavity of the apparatus, transmits electronic signals indicative of weights of a sample before and after volatilization of water and other volatiles therefrom, through preamplifier and filter 61 and analog/digital converter 63 to input/output 43. Microprocessor 45, which receives electronic signals through input/output unit 43 from analog/digital converter 63 and peripheral interface 47, calculates the volatiles or solids content by weight loss. Peripheral interface 47 is usually either a serial transmission device, commonly referred to in the trade as an RS-232 type data transmission system, or a parallel data transmission device, commonly referred to as a BCD data (binary coded decimal) transmission system. The serial RS-232 system is preferred. The microcomputer may also contain other chips, incorporating other formulas for fat content, and other chips for different modes of operation, e.g., moisture content, protein content, etc., of other materials, may also be included. In response to a signal from operator keyboard 35 display 65 may report the final answer, percentage fat present, or may include operational instructions. Instead of a visual display an audio report and audio instructions may be given, or the printer may be utilized.

In FIG. 3 which resembles FIG. 3 of U.S. Pat. No. 3,523,446, hollow glass U-tube 67, in which the sample to be tested for density is present during the test, is connected by inlet and outlet glass tubing (only inlet tubing 69 is shown) to a source of sample to be tested. Line 69, shown supported by a wall 71, communicates with an inlet for insertion of a sample into U-tube 67 (only one side of the U is shown) but the usual means employed for inserting the sample into the tubing (a syringe and a tubing seal) are not illustrated. Also not illustrated is a drain from the return tubing (not shown) to a waste holding pan (not shown) which facilitates insertion of sample into the U-tube free of air. The oscillator illustrated incorporates a small rod-like, permanent magnet 73, which can be inserted into two opposed coils 75 and 77. Coil 77 which constitutes a pick-up coil, is connected to coil 75, a driver coil, by excitation amplifier 79.

More details about the automatic volatility computer and the electronic density measuring apparatus of this invention and their operations will now be given. While the temperature controller is important to the proper operation of the invention it is considered that its function is apparent from the drawing in the previous description. However, the volatility computer and density measurer are more complex units and will be described further.

The density measuring apparatus 13, as illustrated, includes a filling access element 81 mounted on a front wall 83. When a sample is to be inserted into the U-tube, which is a part of the mechanical oscillator formation of the density apparatus (such formation includes the oscillating means, the U-tube and the sample contents of the U-tube) a tempered sample, at desired temperature, is transferred from vial 23 to a syringe, not shown, and is then inserted by means of the syringe into U-tube 67 through line 69. During such insertion about five milliliters of the normal ten milliliters content of the vial are taken into the syringe and about four milliliters of this are discharged into inlet tube 69, with about 0.7 ml. remaining in and filling the U-tube, and with the rest exiting from it through the outlet line corresponding to inlet 69, and through a drain outlet, not shown, into a waste pan, not illustrated. Due to the operation of the density measuring apparatus, which is more fully described in U.S. Pat. No. 3,523,446, issued to O. Kratky et al., which is hereby incorporated by reference, the resonant period of the test sample, compared to a base material, such as water, is related to and is indicative of the mass of the sample in the U-tube, and therefore relates to the density of the sample (because the U-tube volume is constant). The resonant period or the period of oscillation is measured and from it the density is computed (a control having been run first so that the difference between the resonant periods of the sample and the control can be measured) and is displayed in display area 85. Other parts of the density apparatus 13 are an on-off switch 85, a blower or air pump (not shown), and connections between the internal digital computer (not shown) and other parts of the apparatus (including interfacing with the volatility computer). The density measuring apparatus illustrated is like that shown and described in the Anton Paar, K.G. instruction manual for their DMA 40 Digital Density Meter, previously mentioned. Because the volatility computer includes a microcomputer the computer of the density measuring apparatus may be dispensed with or omitted, with the connections from the mechanical oscillator formation being made directly to the automatic volatility computer microprocessor through peripheral interface 47 (FIG. 2).

Other components of the automatic volatility computer 11 include a door 87, handle 89, on-off switch 91 and louvers 93. Not specifically illustrated are a weighing stem, supporting a weigh pan on which the sample rests, usually between two pieces of filter paper, the magnetron, and known circuitry for operation of the magnetron and for recording the weights on the weigh pan, including tare weight, weight with sample before microwave drying and weight with sample after microwave drying. The automatic volatility computer employed may be that described in the CEM Corporation bulletin entitled Moisture/Solids Analyzer, AVC-80 and in the CEM Corporation operation and service manual entitled Automatic Volatility Computer, Model AVC TM -80, both of which were previously referred to in this specification. Such an automatic volatility computer is described in U.S. Pat. No. 3,909,598, previously mentioned.

The described apparatus may be assembled from a CEM Corporation AVC-80 Automatic Volatility Computer (with built-in computer), a CEM Serial Dot Matrix Printer, 80 Column, a Paar DMA 40 Digital Density Meter of the type described in the instruction manual previously referred to and in a four-page publication entitled Digital Density Meter for Liquids and Gases, DMA 40 (which density meter may be suitably modified, as by moving the sample inlet to the front thereof, or may have only the mechanical oscillator formation employed), or a Paar DPA 2000 Density Meter, and a suitable water bath, such as Exacal Model EX-100B. The density meter and the AVC-80 are electronically connected together, using serial or parallel data transmission. When the equipment has been set up, with the proper chip or integrated circuitry in the AVC-80 unit to allow computation of the fat content of the product from its density and moisture content (this is mode no. 7 of the AVC-80 unit employed), the evaluations of samples of dairy products (or comparable other materials) for fat content (or other component for which the analytical technique is suitable) may begin.

The following description of the apparatus and the process of this invention will be with respect to determining the fat content of raw milk but it must be understood that various other dairy products, as well as other materials of properties such that they may be analyzed by the present system, may also be the subject of the present invention. For example, among the dairy products one may also analyze pasteurized milk, homogenized milk, cream, "half-and-half", evaporated milk, condensed milk, ice cream and ice cream mixes, and cottage cheese and other cheeses. Materials that are normally in solid state are appropriately converted to liquids, either by heating or by employment of a suitable solvent in known proportion. In some instances, materials that are in the solid state may be finely divided and employed as suspensions. The present invention, while primarily directed to fat analyses of milk and other dairy products, is also applicable to analyses of other foodstuffs, such as meats, meat products, mayonnaises, salad dressings, margarines, diet margarines and other fatty materials. In some instances the invented method may be adaptable for protein determinations or determinations of other materials present, sometimes by difference. Instead of the Paar type density meter being employed other devices for determining density which can be modified to emit a characteristic electrical signal for the density may also be utilized. While the invented technique, as described, is so easy to practice in a short time, so that results are often obtainable within five or ten minutes or less, exclusive of preliminary heating or tempering, and very often will be routinely obtained within 2 to 4 minutes, the invention can also be applicable to continuous determinations of density, with the appropriate electrical signals being sent to the AVC-80 volatility analyzer continuously or at the moment desired, for fat content determinations. Also, although particular formulas for fat determination for various materials will be given in this description, which formulas are incorporated in the software in an AVC-80 chip (or a plurality of such chips), it is understood that other such formulas may also be derived and used for fat content determinations and for analyses for other components of materials, and such are also within the present invention.

To start the operation of the density meter, after measuring the density of water or other base liquid with the apparatus, the sample or samples of materials to be tested, in liquid state, are tempered or heated in the described water bath to a suitable temperature, sometimes the same as or slightly higher, e.g., 1° to 10° C. or 1° to 5° C. higher, than the temperature at which the sample is to be maintained in the density meter. However, usually the sample is heated to the same temperature as that which is maintained in the mechanical oscillation formation. Normally such temperature in the density meter will be from 20° to 55° or 60° C., preferably 30° to 50° C. and more preferably 35° to 45° C., e.g., about 40° C., for most dairy products. Higher than about 40° C. one will take care to avoid product separation, which can occur after about 8 to 20 minutes heating. The reason for tempering to a higher temperature, when such is practiced, is to thin the sample so that any entrapped air may escape. The analytical technique is independent of viscosity and does not require measuring out a particular volume or weight of sample but it can be sensitive to the presence of air bubbles in the product because they occupy volume and thereby decrease the mass of the sample in the tube or other container of the mechanical oscillator formation. While tempering to a temperature higher than the density testing temperature may be theoretically desirable, as a practical matter it has been found that such is not required to obtain accurate fat analyses. If the tempering temperature is higher than the temperature at which the oscillator formation is to be maintained the sample is soon cooled to such temperature after insertion into the oscillator formation container, due to circulation about it of the water or other fluid from the temperature controller. After the test sample is at the desired temperature for insertion into the oscillator formation a sample is drawn into a syringe from a sealed vial thereof and is injected into the oscillator formation tube. Because such tube is of relatively small volume, normally being from 0.5 to 1 ml., excess sample passes through the tube, eliminating any gas contained therein or in the lines, and some is intentionally left in the syringe, so that no air enters the tube from the syringe. A numeral related to the density of the sample (the resonant period) will be displayed by the density meter and/or by the display of the AVC-80 or other computer. When such numeral is constant and when the solids determination by the AVC-80 has been completed the percentage of solids content and the percent fat will be displayed by the AVC-80 or other computer and/or printed by the printer. Prior to injection of the test sample into the density meter a similar run would have been made using water at the same temperature as would be employed for the sample. When the resonant period or frequency reading characteristic of the density of the water is constant that figure is entered into the computer and the difference between it and the reading for the sample is that which is relatable to the difference between the densities of the sample and water.

After completion of a run water or other suitable cleaning liquid is injected into the density meter so as to clean out any material present in it. Repeated injections may be employed. Normally it is preferred to follow the water injection(s) with one of a cleaning material, which may include a volatile constituent to promote drying of the U-tube by air or other gas, which is subsquently passed through such tube, and the lines to and from it, to promote rapid drying thereof. Such cleaning and drying operations facilitate rapid density determinations by the density meter without the need for removing the sample tube from it, and it has been found by repeated experiments that such cleaning operation is entirely satisfactory and the fat content readings obtained are accurate.

The operation of the AVC-80 or other automatic volatility computer is essentially the same as has been described for such apparatuses in the materials incorporated herein by reference, except for the fact that data from the density meter are also processed in the computer and are displayed. After taring of the weight pan, support stem and filter papers or other materials on which the sample is placed (or between which it is placed), the sample (of the same composition as that, the density of which is being determined in the density meter), preferably at a temperature of about 1° to 10° C. (up to room temperature may also be employed), is placed on one piece of filter paper and sandwiched between such paper and another, and is positioned on the weigh pan. The low temperature is to aid in preventing evaporation of volatiles before the first weighing. The weight is read and displayed by the computer, and the difference is stored in the computer memory. The power input and time of operation are then set and the unit is started, with the microwave radiation heating the sample and evaporating moisture and any volatile materials from it, and with most of the material removed being moisture. By regression analysis techniques, which will be referred to subsequently, relations between solids content (or moisture or volatile material content) and density (represented by the resonant period or frequency) have been accurately related to fat contents for various dairy products. Thus, when the drying operation of the AVC-80 is complete the computer, on command, will display both the percent solids (or moisture or volatiles) and the fat content of the sample, and will print these, if desired. Normally the time employed to dry the sample in the AVC-80 will be from 2 to 6 minutes, preferably 2 to 4 or 5 minutes, e.g., 3½ minutes, and the power input will preferably be from 80 to 95%, more preferably 88 to 92%, e.g., 90%. With such drying times and power inputs it is found that the drying operation can be quickly and completely effected without burning the sample or causing decomposition of components thereof.

The formulas in the computer for fat contents of four materials, determined by regression analysis, will be given below. Other formulas have also been developed for other dairy products, such as cottage cheese, condensed milk, pasteurized milk, reconstituted milk from milk powder, and butter but it is considered that the four formulas are representative and sufficiently illustrate the invention. For raw milk the percent of fat therein, $$F_r = 100\left[\frac{0.86427\ (\%\ \text{solids})}{100} - 2.48999\ (T_s - T_w) + 0.00040\right],$$

wherein $T_s$ is the period of resonant oscillation (resonant period) for the sample and $T_w$ is the resonant period for the water, both being tempered to the same temperature (40° C.). Corresponding formulas for the fat contents (percentages) of cream, ice cream mix and condensed milk, respectively, are $$F = 100\left[\frac{0.86852\ (\%\ \text{solids})}{100} - 1.36234\ (T_s - T_w) - 0.01688\right],$$

$$F = 100\left[\frac{0.70708\ (\%\ \text{solids})}{100} - 1.55736\ (T_s - T_w) + 0.00033\right]\ \text{and}$$

$$F = 100\left[\frac{0.58858\ (\%\ \text{solids})}{100} - 1.34632\ (T_s - T_w) + 0.01451\right].$$

The formulas given were obtained by regression analyses based on a preliminary assumption that for the described products the product density is a function of the densities of three main components, fat, water and other materials (mainly protein and sugar), and the percentages thereof present. Although the "other materials" include both water soluble and water insoluble compounds it has been found that the derived relationships give accurate fat analyses. In a similar manner formulas relating volatiles content (or solids content) to contents of other components of other products, which components are of different densities, may be derived and the analyses of such products may be undertaken in similar manner.

Because the density measuring (or resonant period measuring) apparatuses that may be employed in the following examples cannot have identical mechanical oscillation characteristics, the relationships set for the above four determinations of fat contents have been established for the particular apparatus employed. Each other apparatus is standardized against the first one, using water and an appropriate "standard sample", which sample is preferably about the density of the product to be analyzed. Thus, for analyses of raw milk, which has a density of about 1.055 g./ml. at 40° C., an aqueous copper sulfate solution of such density (about 9%) is employed as the "test sample". In such case, if, for example $T_s - T_w$ for the standard copper sulfate solution and water, measured by the first apparatus, was 0.0283943, and if for the second apparatus it was 0.0278512 the computer of the AVC-80 apparatus used with the second density measurer would be programmed at the factory to "correct" the $(T_s - T_w)$ by multiplying by 0.0283943/0.0278512, or 1.0195. Using such a correction factor the same equations for fat content may be used for all the apparatuses, which is an important attribute of the invention.

The following examples illustrate but do not limit the invention. Unless otherwise indicated, all parts are by weight and all temperatures are in °C. in the examples and throughout the specification.

EXAMPLE 1

The temperature controller is set at 40° C. for both the water circulating to the density meter and for the tempering water used to raise the temperature of sealed vials of test samples of dairy products. The AVC-80 volatility computer and the density meter are turned on, and after heating of the temperature controlled water to 40° C., it is circulated through the density meter and is also employed to raise the temperature of the sealed vials of samples to 40° C. Although the vials are sealed provision is made to allow the escape of any dissolved gas therein. It takes about 5 to 7 minutes for the temperature of the samples to be raised to 40° C. When the AVC-80 digital display is turned on the mode is set for Section No. 7 and the display reads Mode Section #7, Solids/Fat Analysis. The date is indicated by 00/00/00 and instructions appear to insert the correct date by means of the keyboard. After the date is inserted the display indicates that the percent of solids will be displayed. The ready button is pressed, at which time the display reads Power, P=%. At this time 90 is inserted by pressing 9 and 0 on the keyboard to set the AVC-80 unit for 90% power. Then time, T=00:00 appears, and for the desired 4 minutes and 30 seconds operation (or 3:30) of the magnetron, 4:30 is pressed. Then the display reads Condensed, Fat Y (Rdy) N (Chg). Because this is not the desired category the change button is pressed. The next display is similar but is for Homogenized, Fat. Again the change button is pressed and the next display is for Raw Milk, Fat. Because this is the type of test being run the Rdy or the Y button is pressed. Next on the display will appear sequentially indications of the constants, which can be changed if desired, but because they were properly set in the computer, they were not changed. Accordingly, for all four constants the ready button is pressed. Note that the fourth constant is not being employed and therefore is zero but provision has been made for further improving the regression formulas by allowing the insertion of a fourth constant, if that should be considered desirable in the future. The display then indicates % Solids Bias, to allow for different fat analyses to be used as comparisons, but no bias is needed, so Rdy is pressed.

Water calibration of the density meter is made at the beginning of each day of operation. Such is begun by pressing the water/solids button of the AVC-80 keyboard. First, the display appears as Cal. Units (Rdy) CU=0.0000. At this point the tempered distilled water, at 40° C., is injected into the U tube of the mechanical oscillator formation of the density meter and two to three minutes is allowed for the temperature thereof to equilibrate to exactly 40° C. The change button is pressed to record the numerical value indicated on the density meter display when it is constant. Such value will normally be within the range of 4.3345 to 4.3342. In the present case it is 4.3344.

The preliminary setting up of the apparatus having been completed, the lab technician now proceeds to analyze one of the samples. Approximately 10 ml. of the sample, which have been heated in a sealed vial in the 40° C. water bath for a minimum of about 5 to 7 minutes (note that several samples may be tempered at the same time), are ready for injection. Meanwhile, because the moisture determination takes longer than the density determination, two filter papers or support pads are placed on the balance of the volatility computer, the door is closed and the tare button is pressed. The sample is then applied to the pads, preferably on one pad and covered by the other, to minimize any spattering during heating, and the Run button is pressed immediately. The computer will display the peak weight reading. The fat analysis is then started on the density meter.

First a small syringe, holding about 5 ml., is filled from the vial of tempered sample. It is inserted slowly into the density meter cell and is not removed during the test. On completion of the solids test the volatility computer will signal audibly. When the digital read-out on the density meter is stable the ready button on the AVC-80 computer is pressed. The computer will then display the results as ___%S___%F, indicating percent solids and percent fat in the sample. Also indicated will be the percent of power capacity used and the time of magnetron actuation. For this run the percentage of solids indicated is 12.45 (87.55%) volatiles, principally moisture) and the percentage of fat is 3.73. $(T_s-T_w)=0.028394$, and the "actual" percentage of fat, as determined by a standard fat analysis technique (Mojonnier), is 3.62%.

The experiment is repeated with 14 other samples and for the fifteen tests the "actual" fat percentages range from 2.57 to 3.84. The percentages obtained by the present method range from 2.55 to 3.85 and the solids contents range from 11.35 to 12.58. The deviations from the actual percentages of fat range from 0.01 to 0.11%, averaging 0.05%. Especially in view of the speed of the determinations, such an average variation is considered highly acceptable. The standard error of fit is 0.3161%.

The formula shown, which is programmed into the computer, is intended for use with raw milk, for which the fat content is within the range of 2.00 to 4.50, usually being from 3.40 to 4.10. The same formula can be used in measuring the fat contents of finished milks, such as 0.5%, 1%, 2%, 3.5% and 4% fat milks, but preferably, for increased accuracies, other equations will be derived for such specific cases.

The following is a tabulation of data for fifteen different samples of raw milk, which proves the accuracy of the present apparatus and process in analyzing for fat contents. Sample No. 1 is that previously described herein.

TABLE 1

| Sample No. | % Solids (AVC-80) | % Fat (Invention) | % Fat (Mojonnier) | Fat Contents Difference (%) |
|---|---|---|---|---|
| 1 | 12.45 | 3.73 | 3.62 | +.11 |
| 2 | 12.44 | 3.73 | 3.62 | +.11 |
| 3 | 12.24 | 3.51 | 3.49 | +.02 |
| 4 | 12.15 | 3.39 | 3.40 | −.01 |
| 5 | 12.23 | 3.65 | 3.66 | −.01 |
| 6 | 12.18 | 3.65 | 3.62 | +.03 |
| 7 | 12.39 | 3.63 | 3.61 | +.02 |
| 8 | 12.33 | 3.70 | 3.65 | +.05 |
| 9 | 12.58 | 3.85 | 3.84 | +.01 |
| 10 | 12.05 | 3.48 | 3.42 | +.06 |
| 11 | 12.05 | 3.49 | 3.44 | +.05 |
| 12 | 12.28 | 3.44 | 3.54 | −.10 |
| 13 | 12.28 | 3.45 | 3.54 | −.09 |
| 14 | 11.35 | 2.55 | 2.57 | −.02 |
| 15 | 11.31 | 2.58 | 2.59 | −.01 |

Between determinations the syringe is removed from density measuring apparatus and the cell thereof is flushed with distilled water and a solvent-containing cleaning solution. Then the air pump, which is included with the density meter apparatus, is actuated to start the drying of the cell (the container of the mechanical oscillator formation). The density meter read-out for the apparatus employed will normally be within the range of 3.2200 to 3.2299 before drying is discontinued. After drying the system is ready for the testing of another sample of the same type or it may be changed to test a different product. To test such a different product the category heading is changed, as was previously described. For instance, in the next example the program is changed to that for cream by pressing the change button until "Cream Fat" shows, after which the ready button is pressed.

EXAMPLE 2

The procedure of Example 1 is followed, with the material tested being cream. In such case the percent solids found is 45.96, the percentage of fat is 40.85 and $(T_s-T_w) = -0.0192377$. The "actual" fat content, determined by solvent extraction and evaporation, is 40.89%. Such determination is repeated for twelve additional samples, and for the thirteen samples the "actual" fat contents range from 31.07% to 44.96% whereas the calculated fat contents by the present method range from 31.12 to 44.82%. The deviations from the actual percentages of fat range from 0.00 to 0.14% and the standard error of fit is 0.1187%. The percentages of solids in the described materials ranged from 35.93% to 49.65%.

Table 2 sets forth the data obtained in this example, using thirteen different cream samples.

TABLE 2

| Sample No. | % Solids (AVC-80) | % Fat (Invention) | % Fat (Mojonnier) | Fat Contents Difference (%) |
|---|---|---|---|---|
| 1 | 45.96 | 40.85 | 40.89 | −.04 |
| 2 | 45.08 | 40.05 | 40.01 | +.04 |
| 3 | 43.29 | 38.38 | 38.43 | −.05 |
| 4 | 42.55 | 37.46 | 37.54 | −.08 |
| 5 | 40.09 | 35.35 | 35.34 | +.01 |
| 6 | 44.47 | 39.32 | 39.32 | 0 |
| 7 | 45.05 | 39.85 | 39.88 | −.03 |
| 8 | 38.29 | 33.28 | 33.18 | +.10 |
| 9 | 38.20 | 33.17 | 33.26 | −.09 |
| 10 | 35.93 | 31.12 | 31.07 | +.05 |
| 11 | 48.29 | 43.51 | 43.49 | +.02 |
| 12 | 41.59 | 36.58 | 36.72 | −.14 |
| 13 | 49.65 | 44.82 | 44.96 | −.14 |

EXAMPLE 3

The procedures of Examples 1 and 2 are repeated, with the materials tested being differently flavored liquid ice cream mixes, chocolate and vanilla. For a chocolate mix the percentage of solids is 41.77 and the percentage of fat is 9.51, compared to a Mojonnier analysis fat content of 9.49%. $(T_s-T_w)$ is 0.128793. The experiment is repeated 14 more times with other samples of chocolate ice cream and for the 15 samples the percentages of solids are found to range from 37.36 to 43.21, whereas the percentages of fat range from 9.51 to 12.56%. The Mojonnier fat contents range from 9.49 to 12.44. The deviation averages 0.06% and the standard error of fit is 0.1591%.

Table 3 gives the data from such experiments.

TABLE 3

| Sample No. | % Solids (AVC-80) | % Fat (Invention) | % Fat (Mojonnier) | Fat Contents Difference (%) |
|---|---|---|---|---|
| 1 | 41.77 | 9.51 | 9.49 | +.02 |
| 2 | 42.46 | 12.56 | 12.44 | +.12 |
| 3 | 37.36 | 9.86 | 9.87 | −.01 |
| 4 | 41.79 | 9.81 | 9.82 | −.01 |
| 5 | 43.17 | 12.12 | 11.96 | +.16 |
| 6 | 41.72 | 11.94 | 11.84 | +.10 |
| 7 | 41.36 | 11.79 | 11.72 | +.07 |
| 8 | 43.21 | 11.83 | 11.85 | −.02 |
| 9 | 41.86 | 11.98 | 12.06 | −.08 |
| 10 | 41.14 | 11.36 | 11.45 | −.09 |
| 11 | 42.17 | 11.26 | 11.33 | −.07 |
| 12 | 41.82 | 9.88 | 9.91 | −.03 |
| 13 | 42.03 | 11.67 | 11.68 | −.01 |
| 14 | 42.27 | 11.99 | 11.90 | +.09 |
| 15 | 42.72 | 12.00 | 12.06 | −.06 |

TABLE 4

| Sample No. | % Solids (AVC-80) | % Fat (Invention) | % Fat (Mojonnier) | Fat Contents Difference (%) |
|---|---|---|---|---|
| 1 | 38.48 | 10.19 | 10.29 | −.10 |
| 2 | 39.78 | 10.73 | 10.73 | 0 |
| 3 | 38.85 | 11.89 | 11.99 | −.10 |
| 4 | 38.85 | 10.40 | 10.30 | +.10 |
| 5 | 39.13 | 11.98 | 11.90 | +.08 |
| 6 | 39.70 | 12.47 | 12.48 | −.01 |
| 7 | 39.85 | 12.18 | 12.16 | +.02 |
| 8 | 38.86 | 12.34 | 12.23 | +.11 |
| 9 | 38.68 | 12.23 | 12.26 | −.03 |
| 10 | 39.36 | 11.83 | 12.00 | −.17 |
| 11 | 38.70 | 12.69 | 12.77 | −.08 |
| 12 | 37.79 | 9.85 | 9.84 | +.01 |
| 13 | 38.75 | 10.26 | 10.27 | −.01 |
| 14 | 38.27 | 10.42 | 10.44 | −.02 |
| 15 | 40.64 | 11.13 | 11.13 | 0 |

EXAMPLE 4

The experiment of Example 3 is repeated, using vanilla ice cream mixes. The same equation is in the computer program as was employed in Example 3. Table 4 gives the data obtained, using fifteen different vanilla ice cream mixes.

It is clear that the invented apparatus and method work equally well on chocolate and vanilla ice cream mixes. This is important because other electronic fat analysis methods, such as infrared techniques, often give erroneous readings for chocolate mixes or require dilutions of such mixes, which are not necessary when practicing the present invention.

EXAMPLE 5

An experiment like those of Examples 1–4 is run on a sample of condensed milk. The solids content is found to be 41.05%, the fat content is found to be 12.53% and $T_s-T_w = 0.09717$. The standard error of fit is 0.1315%.

In Table 5 the data from fifteen runs on different condensed milk samples are given, confirming the practicality of the invented apparatus and method for analyzing such product for fat content.

TABLE 5

| Sample No. | % Solids (AVC-80) | % Fat (Invention) | % Fat (Mojonnier) | Fat Content Difference (%) |
|---|---|---|---|---|
| 1 | 41.05 | 12.53 | 12.35 | +.18 |
| 2 | 41.20 | 12.56 | 12.46 | +.10 |
| 3 | 41.75 | 12.45 | 12.41 | +.04 |
| 4 | 40.50 | 12.28 | 12.37 | −.09 |
| 5 | 41.64 | 12.72 | 12.78 | −.06 |
| 6 | 41.40 | 12.60 | 12.67 | −.07 |
| 7 | 41.39 | 12.58 | 12.68 | −.10 |
| 8 | 43.16 | 13.47 | 13.44 | +.03 |
| 9 | 43.16 | 13.44 | 13.48 | −.04 |
| 10 | 42.95 | 13.09 | 12.95 | +.14 |
| 11 | 41.84 | 12.64 | 12.60 | +.04 |
| 12 | 42.95 | 13.04 | 12.99 | +.05 |
| 13 | 37.94 | 11.57 | 11.66 | −.09 |
| 14 | 40.59 | 12.15 | 12.22 | −.07 |
| 15 | 36.46 | 11.21 | 11.24 | −.03 |

When the products to be tested are not in flowable liquid state at room temperature they can be liquefied by melting, dissolving or emulsifying, and immiscible liquids and/or solids may be homogenized so that they can be added as a liquid to the oscillation cell. Such technique is often useful for analyzing cheeses, spreads, peanut butter and butter. In addition to the dairy products illustrated the invention is applicable to other foods, such as meats, salad dressings and food emulsions, and may also be used to determine contents of components of non-food materials, such as oil-in-water and water-in-oil emulsions and creams, e.g., cosmetic lotions and face creams. It will be evident that in all the experiments, in the specification and in the claims the analyses of fats include oils too, and the word "fat" includes various lipophilic materials, including oils (which may be considered to be normally liquid fats).

The advantages of this invention have been referred to elsewhere in the specification and will be obvious to one of skill in the art from it and the reported working examples. The apparatus is simple to use and is trouble-free. The procedures followed allow rapid determinations of fat contents of dairy products and such determinations are of acceptable accuracy in practical applications of the invention. The equipment can be employed without the need for extensive training of the operator. Thus, the invention allows determinations of fat (and oil) contents of materials, such as raw milk, upon the fat content basis of which the farmer is paid, and dairy products, which are produced to certain fat content standards. Thus the apparatus, which can readily be made mobile and can be employed in the field, as well as in the factory or dairy, provides a rapid means of determining fat (and oil) contents of products without the need to employ less accurate, more time consuming and less convenient test methods, such as the Babcock, Gerber, and Mojonnier or Roese-Gottlieb methods, and without using the solvents and reagents normally employed in such tests. Also, the equipment is considered to be more accurate, faster and easier to operate than other "electronic" apparatuses, such as the infrared absorption analyzer, the near infrared reflectance analyzer and the Milko turbidometric tester. The infrared and turbidity devices can operate satisfactorily in analyzing milk but they are inaccurate for fat analyses of cream and ice cream mixes and are susceptible to error when strong colorants or cell coating components are present. Also, changes in fat globule sizes can affect the analytical results and often a minor change in a component of a product can cause significant inaccuracies in an analysis. Furthermore, the turbidometric technique is limited to fat analyses whereas the present invention has a wider use potential.

The invention has been described with respect to various illustrative embodiments and working examples but it is not to be limited to these because it is evident that one of skill in the art, with the present specification before him or her, will be able to utilize substitutes and equivalents without departing from the invention.

What is claimed is:

1. An apparatus for determining the fat content of a food which comprises means for automatically measuring a density characteristic of a food and producing an electronic signal corresponding to the density of the food, means for automatically measuring a solids content characteristic of a food and producing an electronic signal corresponding to the solids content of the food, computer means to determine the fat content of the food from the electronic signals, means for transmitting the electronic signals to the computer means, and means for reporting the fat content of the food.

2. An apparatus according to claim 1 wherein the food, the fat content of which is to be determined, is in liquid state during measurement of the density characteristic thereof, the means for automatically producing an electronic signal corresponding to the density of the food includes a mechanical oscillator formation containing therein a sample of the food, the density of which is to be determined, and means for determination of the resonant frequency or period of such mechanical oscillator formation, and the means for automatically producing an electronic signal corresponding to the solids content of the food includes means for weighing a sample of the food, means for subjecting such sample to microwave radiation to remove volatile material therefrom and means for weighing the sample after removal of the volatile material from it.

3. An apparatus according to claim 2 wherein the food is a dairy product, the means for determining the resonant frequency or period of the mechanical oscillator formation includes an excitation amplifier, and the apparatus comprises means for maintaining constant the temperature of a liquid state dairy product in the means for automatically producing an electronic signal corresponding to the density thereof.

4. An apparatus according to claim 3 wherein the food is a normally liquid dairy product and the means for automatically producing an electronic signal corresponding to the solids content of the dairy product is an automatic volatility computing apparatus which includes numeric and function imput keys and a display on which the percentage of fat in the sample of dairy product is displayed, as determined by the computer from the electronic signals corresponding to the density and the solids content of the dairy product.

5. An apparatus according to claim 4 wherein the automatic volatility computing apparatus includes integrated circuitry to adapt a microprocessor thereof to calculate the fat contents of different dairy products from the electronic signals corresponding to the density and the solids contents thereof, and the means for producing an electronic signal corresponding to the density of a dairy product comprises a syringe receiving inlet to the mechanical oscillator formation to receive the sample of dairy product in liquid state, pump means for circulating water at a controlled temperature about the mechanical oscillator formation to maintain the temperature thereof constant, and means for selectively circulating a cleaning liquid and a drying gas through a container of the mechanical oscillator formation to selectively clean and dry it between fat content determinations.

6. An apparatus according to claim 5 comprising temperature controlling means for maintaining a desired constant temperature of a fluid which is circulated from such means to the means for automatically producing an electronic signal corresponding to the density of the dairy product to maintain the mechanical oscillator formation at desired constant temperature, which temperature controlling means includes holding means for containers of samples of dairy products for which the fat content is to be determined, which dairy products, in liquid state, are thereby held at desired temperature for syringe charging to the mechanical oscillator formation.

7. An apparatus according to claim 1 wherein the computer means are selectively capable of automatically determining the fat content of any of a plurality of foods from the electronic signals because such computer has included therein a plurality of selectively actuatable equations or programs for determining the fat content of any of such plurality of foods from electronic signals corresponding to densities and solids contents thereof.

8. An apparatus according to claim 6 wherein the computer is selectively capable of automatically determining the fat content of either of at least two foods of a group consisting of milk, cream, ice cream mixes, condensed milk, butter and cottage cheese because of the inclusion in the computer of selectively actuatable equations for determining such fat contents from electronic signals from the automatic density meter and volatility computer corresponding to densities and solids contents thereof.

9. A process for determining the fat content of a food which comprises automatically measuring a density characteristic of a food and producing an electronic signal corresponding to the density of the food, automatically measuring a solids content characteristic of a food and producing an electronic signal corresponding to the solids content of the food, transmitting the electronic signals to a computer, automatically computing with the computer the fat content of the food from the electronic signals, and reporting the fat content of the food.

10. A process according to claim 9 wherein the food, the fat content of which is to be determined, is in liquid state during measurement of the density characteristic thereof, the electronic signal corresponding to the density of the food is produced by a process including measurement of the resonant frequency or the period of oscillation at resonant frequency of a mechanical oscillator formation containing therein a sample of the food, the electronic signal corresponding to the solids content of the food is produced by a process including weighing a sample of the food, subjecting such sample to microwave radiation to remove volatile material therefrom and weighing the sample after removal of the volatile material from it, and automatically computing the fat content of the food from the electronic signals transmitted to the computer, with the determination being made within a period of ten minutes.

11. A process according to claim 10 wherein the food is a dairy product, the sample of dairy product is tempered to desired temperature, after which it is injected by means of a syringe into a container portion of the mechanical oscillator formation, the sample is maintained at desired temperature by means of a circulating heat transfer fluid, the period of oscillation at resonant frequency of the mechanical oscillator containing the sample of dairy product, in liquid state, is measured, compared to the resonant frequency of a control liquid, and the fat content of the dairy product is computed in a microprocessor, utilizing integrated circuitry selectively containing different equations for calculating fat contents of different foods, and the determination of fat content, exclusive of tempering or pre-heating the sample for density measurement, is less than 5 minutes.

12. A process according to claim 11 wherein the dairy product, the fat content of which is to be determined, is in normally liquid state, the density measurement is conducted at a temperature in the range of 20° to 55° C., and after measurement of the density characteristic of the dairy product the container of the mechanical oscillator formation is cleaned by circulation of a cleaning liquid through it and is dried by gas drying, without dismantling of the mechanical oscillator formation.

13. A process according to claim 11 wherein the dairy product is milk, the density measurement is conducted at a temperature in the range of 35° to 45° C. and the determination of the fat content of the sample of the milk being tested takes from 2 to 4 minutes, exclusive of tempering or pre-heating the sample for density measurement.

14. A process according to claim 11 wherein the fat contents of a plurality of different dairy products are measured sequentially, utilizing different programmed equations of the integrated circuitry for calculating them, and such determinations of fat contents, exclusive of temperings or pre-heatings of the samples for density measurements, take less than 5 minutes each.

15. A process according to claim 9 wherein any of a plurality of foods is analyzed for fat content by selective actuation of the computer to solve an equation from a plurality of equations stored in the computer, which is appropriate to determine the fat content of a particular type of food sample being analyzed.

16. A process according to claim 14 wherein the fat contents of the different dairy products are measured by actuation of appropriate equations, stored in the computer, which are suitable for calculating the fat contents of the different dairy products.

17. An apparatus for determining the content of a component of a material, which component is of a different density from other components of the material, which comprises means for automatically measuring a density characteristic of the material and producing an electronic signal corresponding to the density of the material, means for automatically measuring a solids content characteristic of the material and producing an electronic signal corresponding to the solids content thereof, computer means to determine the content of the component of the material from the electronic signals, means for transmitting the electronic signals to the computer means, and means for reporting the component content of the material.

18. A process for determining the content of a component of a material, which component is of a different density from other components of the material, which comprises automatically measuring a density characteristic of the material and producing an electronic signal corresponding to the density of the material, automatically measuring a solids content characteristic of the material and producing an electronic signal corresponding to the solids content thereof, transmitting the electronic signals to a computer, automatically computing with the computer the component content of the material from the electronic signals, and reporting the component content of the material.

* * * * *